(12) United States Patent
Strong

(10) Patent No.: US 12,714,495 B2
(45) Date of Patent: Aug. 25, 2026

(54) SYSTEM FOR IRREVERSIBLE ELECTROPORATION

(71) Applicant: St. Jude Medical, Cardiology Division, Inc., St. Paul, MN (US)

(72) Inventor: Mark Strong, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 709 days.

(21) Appl. No.: 17/928,369

(22) PCT Filed: Jun. 2, 2021

(86) PCT No.: PCT/US2021/035494

§ 371 (c)(1),
(2) Date: Nov. 29, 2022

(87) PCT Pub. No.: WO2021/247738

PCT Pub. Date: Dec. 9, 2021

(65) Prior Publication Data

US 2023/0200893 A1 Jun. 29, 2023

Related U.S. Application Data

(60) Provisional application No. 62/704,920, filed on Jun. 3, 2020.

(51) Int. Cl.
*A61B 18/14* (2006.01)
*A61B 18/00* (2006.01)

(52) U.S. Cl.
CPC .................... *A61B 18/1492* (2013.01); *A61B 2018/00351* (2013.01); *A61B 2018/00613* (2013.01);

(Continued)

(58) Field of Classification Search
CPC ............ A61B 18/1206; A61B 18/1492; A61B 2018/00351; A61B 2018/00613;

(Continued)

(56) References Cited

U.S. PATENT DOCUMENTS 5,769,872 A 6/1998 Lopin
6,326,177 B1 12/2001 Schoenbach (Continued)

FOREIGN PATENT DOCUMENTS

AU 2004311842 C1 1/2011
AU 2010214761 B2 12/2012

(Continued)

OTHER PUBLICATIONS

Parital European Search Report and Written Opinion issued in European Patent Application No. 22189455.3, dated Jan. 2, 2023, 15 pages.

(Continued)

*Primary Examiner* — Tigist S Demie
(74) *Attorney, Agent, or Firm* — Dentons Durham Jones Pinegar

(57) ABSTRACT

Disclosed herein is an electroporation system including a catheter shaft, at least one electrode coupled to the catheter shaft at a distal end thereof, and a signal generator. The signal generator is coupled in communication with the at least one electrode. The signal generator supplies a biphasic pulse to the at least one electrode, the biphasic pulse including a first phase having a first polarity, a first initial voltage amplitude, and a first pulse width. The biphasic pulse includes a second phase having a second polarity opposite to the first polarity, a second initial voltage amplitude, and a second pulse width, wherein at least one of the first initial voltage amplitude or the first pulse width is different from the second initial voltage amplitude or the second pulse width, respectively. A leading edge of the second phase occurs after an interphase delay following a trailing edge of the first phase.

26 Claims, 6 Drawing Sheets

(52) U.S. Cl.
CPC ............... *A61B 2018/00726* (2013.01); *A61B 2018/0075* (2013.01); *A61B 2018/00767* (2013.01)

(58) Field of Classification Search
CPC .. A61B 2018/00726; A61B 2018/0075; A61B 2018/00767; A61B 2018/1246; A61B 2018/126; A61B 2018/1407; A61B 2018/1467
See application file for complete search history.

(56) References Cited

U.S. PATENT DOCUMENTS

| | | | | |
|---|---|---|---|---|
| 6,547,786 | B1 | 4/2003 | Goble | |
| 7,263,397 | B2 | 8/2007 | Hauck | |
| 7,306,940 | B2 | 12/2007 | Miklavcic | |
| 7,536,218 | B2 | 5/2009 | Govari | |
| 8,048,067 | B2 | 11/2011 | Davalos | |
| 8,221,411 | B2 | 7/2012 | Francischelli | |
| 8,251,986 | B2 | 8/2012 | Chornenky | |
| 8,282,631 | B2 | 10/2012 | Davalos | |
| 8,822,222 | B2 | 9/2014 | Beebe | |
| 8,903,488 | B2 | 12/2014 | Callas | |
| 8,926,606 | B2 | 1/2015 | Davalos | |
| 9,113,911 | B2 | 8/2015 | Sherman | |
| 9,283,051 | B2 | 3/2016 | Garcia | |
| 9,289,606 | B2 | 3/2016 | Paul | |
| 9,764,145 | B2 | 9/2017 | Callas | |
| 9,788,885 | B2 | 10/2017 | Long | |
| 9,918,790 | B2 | 3/2018 | Zemlin | |
| 9,956,301 | B2 | 5/2018 | Bhaskaran | |
| 9,956,391 | B2 | 5/2018 | Weissberg | |
| 9,987,081 | B1 | 6/2018 | Bowers | |
| 10,016,232 | B1 | 7/2018 | Bowers | |
| 10,117,701 | B2 | 11/2018 | Davalos | |
| 10,130,819 | B2 | 11/2018 | Callas | |
| 10,136,829 | B2 | 11/2018 | Deno | |
| 10,188,449 | B2 | 1/2019 | Gilbert | |
| 10,238,447 | B2 | 3/2019 | Neal, II | |
| 10,271,893 | B2 | 4/2019 | Stewart | |
| 10,292,755 | B2 | 5/2019 | Arena | |
| 10,322,286 | B2 | 6/2019 | Viswanathan | |
| 10,433,906 | B2 | 10/2019 | Mickelsen | |
| 10,448,989 | B2 | 10/2019 | Arena | |
| 10,470,822 | B2 | 11/2019 | Garcia | |
| 10,512,779 | B2 | 12/2019 | Viswanathan | |
| 10,531,914 | B2 | 1/2020 | Stewart | |
| 10,548,665 | B2 | 2/2020 | Xiao | |
| 10,569,081 | B2 | 2/2020 | Howard | |
| 10,722,302 | B2 | 7/2020 | Sherman | |
| 10,750,975 | B2 | 8/2020 | Hill | |
| 10,849,678 | B2 | 12/2020 | Onik | |
| 2004/0154183 | A1 | 8/2004 | Kim | |
| 2004/0236376 | A1 | 11/2004 | Miklavcic | |
| 2008/0027428 | A1 | 1/2008 | Palanker | |
| 2008/0187013 | A1 | 8/2008 | Guenter | |
| 2009/0059987 | A1 | 3/2009 | Walker | |
| 2010/0261994 | A1 | 10/2010 | Davalos | |
| 2011/0054460 | A1 | 3/2011 | Gilbert | |
| 2012/0116288 | A1 | 5/2012 | Miklavcic | |
| 2013/0030430 | A1 | 1/2013 | Stewart et al. | |
| 2015/0150618 | A1 | 6/2015 | Onik | |
| 2015/0327944 | A1 | 11/2015 | Neal, II | |
| 2016/0051324 | A1 | 2/2016 | Stewart | |
| 2016/0058493 | A1 | 3/2016 | Neal, II | |
| 2016/0331441 | A1 | 11/2016 | Konings | |
| 2016/0367310 | A1 | 12/2016 | Onik | |
| 2017/0035499 | A1* | 2/2017 | Stewart | A61B 18/1492 |
| 2017/0065339 | A1 | 3/2017 | Mickelsen | |
| 2017/0189096 | A1 | 7/2017 | Danziger | |
| 2017/0189097 | A1 | 7/2017 | Viswanathan | |
| 2017/0246455 | A1 | 8/2017 | Athos | |
| 2017/0266438 | A1 | 9/2017 | Sano et al. | |
| 2017/0319851 | A1 | 11/2017 | Athos | |
| 2017/0348525 | A1 | 12/2017 | Sano | |
| 2018/0014751 | A1 | 1/2018 | Hill | |
| 2018/0042674 | A1 | 2/2018 | Mickelsen | |
| 2018/0043153 | A1 | 2/2018 | Viswanathan | |
| 2018/0050215 | A1 | 2/2018 | Pakhomov | |
| 2018/0071014 | A1 | 3/2018 | Neal | |
| 2018/0161086 | A1 | 6/2018 | Davalos et al. | |
| 2018/0214202 | A1 | 8/2018 | Howard | |
| 2018/0221078 | A1 | 8/2018 | Howard | |
| 2018/0303543 | A1 | 10/2018 | Stewart | |
| 2019/0030328 | A1 | 1/2019 | Stewart | |
| 2019/0046255 | A1 | 2/2019 | Davalos | |
| 2019/0060632 | A1 | 2/2019 | Asirvatham | |
| 2019/0117113 | A1 | 4/2019 | Curran | |
| 2019/0125439 | A1 | 5/2019 | Rohl | |
| 2019/0143106 | A1 | 5/2019 | DeWitt | |
| 2019/0183378 | A1 | 6/2019 | Mosesov | |
| 2019/0192223 | A1 | 6/2019 | Rankin | |
| 2019/0201688 | A1 | 7/2019 | Olson | |
| 2019/0223938 | A1 | 7/2019 | Arena | |
| 2019/0232048 | A1 | 8/2019 | Latouche | |
| 2019/0233809 | A1 | 8/2019 | Neal, II | |
| 2019/0256839 | A1 | 8/2019 | Neal, II | |
| 2019/0282294 | A1 | 9/2019 | Davalos | |
| 2019/0328446 | A1 | 10/2019 | Callas | |
| 2019/0350647 | A1 | 11/2019 | Ramberg | |
| 2019/0351224 | A1 | 11/2019 | Sano | |
| 2019/0376055 | A1 | 12/2019 | Davalos | |
| 2020/0000506 | A1 | 1/2020 | Fähsing | |
| 2020/0093541 | A9 | 3/2020 | Neal, II | |
| 2020/0107879 | A1 | 4/2020 | Stewart | |
| 2020/0138334 | A1 | 5/2020 | Hill | |
| 2020/0138506 | A1* | 5/2020 | Fraasch | A61B 18/1206 |
| 2020/0147371 | A1 | 5/2020 | Pakhomov | |
| 2020/0289188 | A1 | 9/2020 | Forsyth | |
| 2020/0289827 | A1 | 9/2020 | Forsyth | |
| 2020/0297418 | A1 | 9/2020 | Stewart | |
| 2020/0298008 | A1 | 9/2020 | Asirvatham | |
| 2020/0315703 | A1 | 10/2020 | Sherman | |
| 2020/0398048 | A1 | 12/2020 | Krimsky | |
| 2020/0405373 | A1 | 12/2020 | O'Brien | |
| 2021/0015549 | A1 | 1/2021 | Haghighi-Mood | |
| 2021/0023362 | A1 | 1/2021 | Lorenzo | |
| 2021/0077030 | A1* | 3/2021 | Viswanathan | A61B 5/308 |
| 2021/0161582 | A1 | 6/2021 | Byrd | |
| 2021/0267672 | A1 | 9/2021 | Tegg | |
| 2022/0133403 | A1 | 5/2022 | Olson | |
| 2022/0226041 | A1 | 7/2022 | Dale | |
| 2022/0304745 | A1 | 9/2022 | Olson | |
| 2022/0378498 | A1 | 12/2022 | Zhang | |

FOREIGN PATENT DOCUMENTS

| | | | |
|---|---|---|---|
| CN | 105731054 | A | 7/2016 |
| CN | 107921258 | A | 4/2018 |
| CN | 108024803 | A | 5/2018 |
| CN | 108778172 | A | 11/2018 |
| CN | 109124760 | A | 1/2019 |
| CN | 109793571 | A | 5/2019 |
| CN | 110573104 | A | 12/2019 |
| CN | 111317557 | A | 6/2020 |
| CN | 111317559 | A | 6/2020 |
| CN | 112022331 | B | 12/2020 |
| CN | 112292090 | A | 1/2021 |
| CN | 112741685 | A | 5/2021 |
| CN | 112969425 | A | 6/2021 |
| EP | 1696812 | B1 | 7/2015 |
| EP | 3232967 | A1 | 10/2017 |
| EP | 3573557 | A1 | 12/2019 |
| EP | 2736434 | B1 | 2/2020 |
| EP | 3614944 | A1 | 3/2020 |
| EP | 3624687 | A1 | 3/2020 |
| EP | 3749238 | A1 | 12/2020 |
| JP | S62275471 | A | 11/1987 |
| JP | H085859 | A | 1/1996 |
| JP | 2017506098 | A | 3/2017 |
| JP | 2018089431 | A | 6/2018 |
| WO | 2007035537 | A2 | 3/2007 |
| WO | 2007059162 | A2 | 5/2007 |
| WO | 2010118387 | A1 | 10/2010 |

(56) References Cited

FOREIGN PATENT DOCUMENTS

| | | | |
|---|---|---|---|
| WO | 2016099774 | A1 | 6/2016 |
| WO | 2018140593 | A1 | 8/2018 |
| WO | 2018200800 | A1 | 11/2018 |
| WO | 2018208795 | A1 | 11/2018 |
| WO | 2019022816 | A1 | 1/2019 |
| WO | 2019108479 | A1 | 6/2019 |
| WO | 2019118436 | A1 | 6/2019 |
| WO | 2019157359 | A1 | 8/2019 |
| WO | 2020051241 | A1 | 3/2020 |
| WO | 2020061192 | A1 | 3/2020 |
| WO | 2020096836 | A2 | 5/2020 |
| WO | 2020096836 | A3 | 6/2020 |
| WO | 2020198796 | A1 | 10/2020 |
| WO | 2020215007 | A1 | 10/2020 |
| WO | 2020227086 | A1 | 11/2020 |
| WO | 2020251857 | A1 | 12/2020 |
| WO | 2021127558 | A1 | 6/2021 |
| WO | 2021236341 | A1 | 11/2021 |
| WO | 2021247738 | A1 | 12/2021 |

OTHER PUBLICATIONS

Search Report Issued in Chinese Patent Application No. 202111047368.X, dated Sep. 15, 2021, 6 pages.

Chinese Search Report issued in related Chinese application No. 202080006215.8, dated Jun. 18, 2021, 9 pages.

International Search Report and Written Opinion for International Patent Application No. PCT/US2020/063039, mailed Feb. 18, 2021, 16 pages.

International Search Report and Written Opinion for International Patent Application No. PCT/US2021/035494, mailed Sep. 16, 2021, 19 pages.

* cited by examiner

SYSTEM FOR IRREVERSIBLE ELECTROPORATION

CROSS-REFERENCE TO RELATED APPLICATIONS

This application claims the benefit of priority to international application No. PCT/US2021/035494, filed Jun. 2, 2021, which claims priority to U.S. Provisional Patent Application No. 62/704,920, filed Jun. 3, 2020, the entire contents and disclosure of which are hereby incorporated by reference herein.

FIELD

The present disclosure relates generally to electroporation systems. In particular, the present disclosure relates to a system and method for delivering biphasic pulsed waveform irreversible electroporation energy.

BACKGROUND

Various therapies are used to treat various conditions afflicting the human anatomy. Cardiac arrhythmias, for example, are sometimes treated using ablation therapy and, more specifically, electroporation. Ablation therapy is a process by which target tissue of a patient is partially or completely damaged. At least some methods of ablation therapy involve the application of an electric field to target tissue by one or more electrodes connected to a signal generator. The one or more electrodes may be incorporated, for example, onto a catheter, or an ablation catheter, that can be navigated to the target tissue. When tissue is ablated using electroporation, the electrodes deliver current to the target tissue to generate an electric field that creates tissue necrosis in cardiac tissue to correct conditions such as atrial arrhythmia (including, but not limited to, ectopic atrial tachycardia, atrial fibrillation, and atrial flutter).

Arrhythmia (i.e., irregular heart rhythm) can create a variety of dangerous conditions including loss of synchronous atrioventricular contractions and stasis of blood flow that can lead to a variety of ailments and even death. It is believed that the primary cause of atrial arrhythmia is stray electrical signals within the left or right atrium of the heart. The ablation catheter imparts ablative energy (e.g., radio frequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Electroporation is a non-thermal ablation technique that involves applying strong electric-fields that induce pore formation in the cellular membrane. The electric field may be induced by applying a relatively short-duration pulse of sufficient amplitude. Such a pulse may be repeated to form a pulse train. When such an electric field is applied to tissue in vivo, the cells in the tissue are subjected to a transmembrane potential that opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation (IRE).

SUMMARY OF THE DISCLOSURE

The present disclosure is directed to systems and methods that deliver biphasic pulsed waveform IRE energy to target tissue in a patient, for example, suffering from a cardiac arrhythmia.

The present disclosure is further directed to an electroporation system including a catheter shaft, at least one electrode coupled to the catheter shaft at a distal end thereof, and a signal generator. The signal generator is coupled in communication with the at least one electrode. The signal generator is configured to supply a biphasic pulse to the at least one electrode, the biphasic pulse including a first phase having a first polarity, a first initial voltage amplitude, and a first pulse width. The biphasic pulse includes a second phase having a second polarity opposite to the first polarity, a second initial voltage amplitude, and a second pulse width, wherein at least one of the first initial voltage amplitude or the first pulse width is different from the second initial voltage amplitude or the second pulse width, respectively. A leading edge of the second phase occurs after an interphase delay following a trailing edge of the first phase.

The present disclosure is further directed to a method of delivering electroporation energy through an ablation catheter. The method includes positioning at least one electrode at a target tissue. The method includes coupling the at least one electrode to a signal generator. The method includes supplying, by the signal generator, a biphasic pulse. Supplying the biphasic pulse includes transmitting a first phase having a first polarity, a first initial voltage amplitude, and a first pulse width. Supplying the biphasic pulse includes supplying zero volt direct current (VDC) for an interphase delay following a trailing edge of the first phase. Supplying the biphasic pulse includes transmitting a second phase having a second polarity opposite the first polarity, a second initial voltage amplitude, and a second pulse width, wherein at least one of the first initial voltage amplitude or the first pulse width is different from the second initial voltage amplitude or the second pulse width, respectively.

BRIEF DESCRIPTION OF THE DRAWINGS

Corresponding reference characters indicate corresponding parts throughout the several views of the drawings. The drawings are not necessarily to scale.

DETAILED DESCRIPTION OF THE DISCLOSURE

Figure 1:
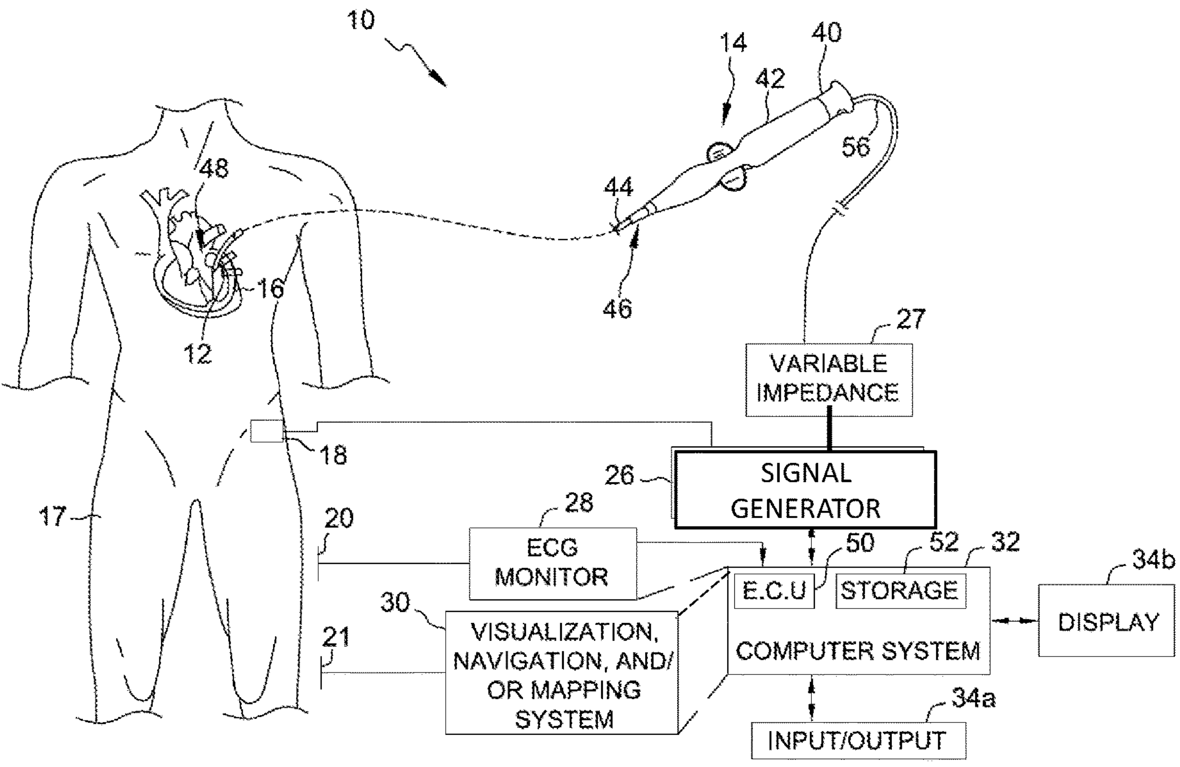
FIG. 1 is a schematic and block diagram view of an example system for delivering electroporation energy.

The systems and methods disclosed herein provide electroporation energy, particularly IRE energy, for application to tissue in the human body. The disclosed systems and methods relate to controlling an electroporation system and, more specifically, a signal generator, to deliver IRE energy to target tissue (e.g., about 400 V/cm to cardiac tissue) to produce more consistent and improved patient outcomes. For example, disclosed embodiments of the signal generator produce biphasic electroporation waveforms, or signals, having specific parameters that differ between the two phases, including, for example, voltage amplitudes or pulse widths. For example, in one embodiment, pulse widths may be substantially equal, but voltage amplitudes differ. In other embodiments, voltage amplitudes may be substantially equal, but pulse widths differ. In yet other embodiments, voltage amplitudes and pulse widths differ. Generally, voltage amplitudes for each phase are in the range of 1 kilovolt (kV) to 3 kV, and pulse widths for each phase are in the range of 100 nanoseconds (ns) to 200 microseconds (us). In certain embodiments, for example, pulse widths are in the range of 5 us to 10 us.

Disclosed embodiments of the signal generator produce the biphasic electroporation waveform, or biphasic IRE waveform, as a "burst," or series, of biphasic "pulses" having an interphase delay between each phase, and an interpulse delay between each biphasic pulse. Interphase delay is generally short to reverse current in target tissue to avoid stimulating other cells, for example, in the range of 100 ns to 100 us. In certain embodiments, interphase delay is in the range of 20 us to 25 us. Interpulse delay between each pulse is generally in the range of 9 us to 50 milliseconds (ms). In certain embodiments, interpulse delay is in the range of 20 us to 50 us. Each burst may include, for example, 1-30 biphasic pulses.

Multiple bursts of biphasic pulses are generated with an interburst delay between each burst. Interburst delay generally is in the range of 270 us to 10 seconds(s). The biphasic IRE waveform, or signal, may include, for example, 1-30 bursts of biphasic pulses. In addition to voltage amplitudes and pulse widths, each biphasic pulse can be partially characterized by their tilt, or the charged capacitive load discharged through the patient load. Because the patient load decays as current is conducted through the tissue, the patient load is supplemented by a charged capacitive load that is discharged over time to maintain an effective patient load in an ideal range for the electroporation system, e.g., between about 25 ohms and 150 ohms. The tilt is exhibited as an initial voltage amplitude of a given phase of the biphasic pulse that decays over the pulse width to an ending voltage amplitude. In certain embodiments, the initial voltage amplitude of a second phase is substantially equal to the ending voltage amplitude of a first phase.

Further, the biphasic waveforms may be generated as inverted or non-inverted by functionally reversing the anode and cathode electrodes. In other words, the biphasic pulse may be positive polarity then negative polarity, or may be negative polarity then positive polarity.

Embodiments of the disclosed systems and methods produce biphasic IRE waveforms to reduce or minimize undesirable skeletal muscle excitation and generation of gasses within a patient, and unintended application of IRE energy to surrounding tissue that is not the intended target of IRE therapy. It is contemplated, however, that the described features and methods of the present disclosure as described herein may be incorporated into any number of electric field-based ablation systems as would be appreciated by one of ordinary skill in the art based on the disclosure herein.

Figure 4:
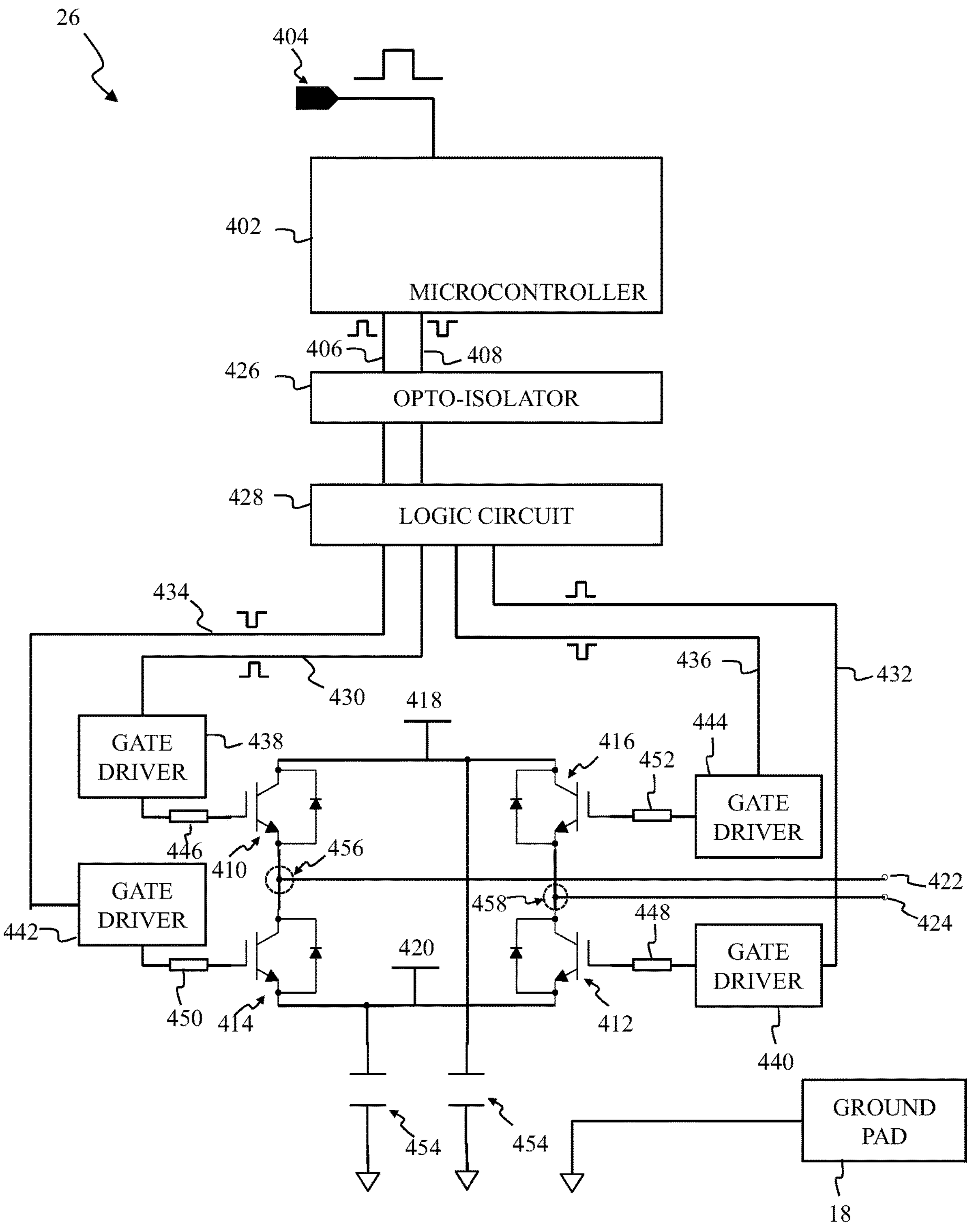
FIG. 4 is a schematic diagram of an example signal generator for use with the system of FIG. 1.

The disclosed systems and methods are generally embodied in an electric field-based ablation system, such as an electroporation system. FIG. 1 illustrates an example embodiment of a system 10 for electroporation therapy and other electrophysiology studies, e.g., mapping, or other ablation therapy. Certain embodiments, such as system 10, include an electrode assembly 12 disposed at the distal end, for example, of a catheter 14. As used herein, "proximal" refers to a direction toward the end of the catheter 14 near the clinician and "distal" refers to a direction away from the clinician and (generally) inside the body of a patient. In alternative embodiments, system 10 may include a plurality of needles having one or more electrodes at their respective distal ends (as shown in FIG. 4). Electrode assembly 12 includes one or more individual, electrically-isolated electrode elements. In some embodiments, each electrode element, also referred to herein as a catheter electrode, is individually wired such that it can be selectively paired or combined with any other electrode element to act as a bipolar or a multi-polar electrode.

System 10 may be used for irreversible electroporation (IRE) to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for plasma membrane electroporation, electric current is delivered as a pulsed electric field in the form of short-duration direct current (DC) pulses between closely spaced electrodes capable of delivering a strong enough electric field to cause irreversible electroporation in the targeted cells. As described in more detail herein, the system 10 is configured to deliver a biphasic IRE waveform, or signal, having a relatively high voltage and low pulse duration as compared to at least some prior electroporation systems. Moreover, the biphasic IRE waveform features phases that may differ in voltage amplitude or pulse width, or both. The waveforms generated by system 10 and applied to catheter electrodes facilitate reducing and/or preventing skeletal muscle stimulation during IRE therapy.

Irreversible electroporation through a multi-electrode hoop catheter may enable pulmonary vein isolation in as few as one shock per vein, which may produce much shorter procedure times compared to sequentially positioning a radiofrequency (RF) ablation tip around a vein. It should be understood that the mechanism of cell destruction in electroporation is not primarily due to heating effects, but rather to cell membrane disruption through application of a high-voltage electric field. Thus, electroporation may avoid some possible thermal effects that may occur when using RF energy. This "cold" or "non-thermal" therapy thus has desirable characteristics.

Catheter electrode assembly 12 includes a plurality of catheter electrodes configured to be used as briefly outlined above and as described in greater detail below. Electrode assembly 12 is incorporated as part of catheter 14 used for IRE and may also be used for sensing, mapping, and diagnostics to conduct electrophysiology studies to identify and treat, for example, arrhythmias. System 10 introduces a modulated electric field into tissue 16 in a body of a patient 17. In the illustrative embodiment, tissue 16 comprises heart or cardiac tissue. It should be understood, however, that embodiments may be used to map, diagnose, or treat a variety of other body tissues. The blood volume and the moving heart wall surface modify the electric field in a manner that can be detected by catheter 14 and, more specifically, electrodes of electrode assembly 12. The electrodes within the heart chamber monitor the modifications to the applied electric field, and the resulting electrical signals enable production of a dynamic representation, e.g., for display to a physician, of the location of the walls of the heart. The electrodes on electrode assembly 12 also detect electrical signals generated by the heart itself. The detected electrical signals can then be displayed, e.g., as an electrocardiogram. System 10, in mapping heart or cardiac tissue, may also be used to locate and navigate a therapy catheter in the heart chamber. In such an embodiment, an electrode on the therapy catheter, which may be incorporated with catheter 14 and electrode assembly 12, or independent, introduces an electric field that can be detected by electrodes on electrode assembly 12. The detected electrical signals enable locating the therapy catheter within the heart.

System 10 enables electroporation therapy to form lesions on target tissue 16. System 10 utilizes electric current in the form a biphasic pulsed electric field in the form of short-duration direct current (DC) pulses between closely spaced electrodes on electrode assembly 12. Pulse widths of these biphasic DC pulses are generally on the order of 100 ns to several hundred microseconds, and the biphasic DC pulses may be repeated with an interpulse delay on the order of several microseconds to tens of milliseconds to form a pulse train, or burst. Such bursts may also be repeated with an interburst delay on the order of hundreds of microseconds to seconds. When a strong electric field is applied to tissue in vivo, the cells in the tissue are subjected to a trans-membrane potential that opens the pores on the cell wall, hence the term electroporation. While the energization strategies for ablation are described as involving DC waveforms, embodiments may use variations or combinations of AC or DC pulses and remain within the spirit and scope of the invention. For example, exponentially-decaying pulses, exponentially-increasing pulses, and combinations thereof may be used. Moreover, while certain embodiments of system 10 are described herein with respect to IRE therapy, it should be understood that system 10 may be used, additionally or alternatively, for other forms of electric field-based ablation therapy.

System 10 further includes a ground pad 18 that provides a ground path, for example, for IRE signals transmitted by a signal generator 26 through electrode assembly 12 and into the body 17 of the patient. FIG. 1 further shows return electrodes 20 and 21 representing body connection for the various sub-systems included in the system 10, such as an electrophysiology (EP) monitor such as an electrocardiogram (ECG) monitor 28, or a visualization, navigation, and/or mapping system 30 for visualization, mapping and navigation of internal body structures.

In the illustrated embodiment, ground pad 18 is a cutaneous patch electrode. Likewise, return electrodes 20 and 21 may also be cutaneous patch electrodes. Ground pad 18 and return electrodes 20 and 21 may include one or more contact configured to attach to the skin. For example, in certain embodiments, the systems and methods described herein may operate with dual contact ground pads, or ground pads having two or more ground contacts. In certain embodiments, ground pad 18 and return electrodes 20 and 21 may be any other type of electrode suitable for use as a return electrode, or ground path, including, for example, one or more catheter electrodes. Return electrodes that are catheter electrodes may be part of electrode assembly 12 or part of a separate catheter (not shown). In some embodiments, for example, system 10 includes a bipolar catheter electrode assembly that includes a plurality of electrode pairs, where each electrode pair includes two electrodes with one electrode functioning as the return electrode.

System 10 may further include a computer system 32 (including an electronic control unit 50 and data storage-memory 52) that, in certain embodiments, may be integrated with visualization, navigation, and/or mapping system 30. Computer system 32 may further include conventional interface components, such as various user input/output mechanisms **34*a* and a display 34*b***, among other components.

System 10 may include a suitable detector and tissue sensing circuit integrated with signal generator 26 or computer system 32 that identify which electrodes of electrode assembly 12 have characteristics (e.g., electrical characteristics such as impedance, phase angle, reactance, etc.) indicative of contact with tissue 16. Signal generator 26, or computer system 32 may then select which electrodes or electrode pairs of electrode assembly 12 to energize based on the electrodes identified as being in contact with tissue 16. Suitable components and methods for identifying electrodes in contact with tissue are described, for example, in U.S. Pat. No. 9,289,606, the disclosure of which is incorporated herein by reference in its entirety.

In the embodiment shown in FIG. 1, catheter 14 includes a cable connector 40, or interface, a handle 42, and a shaft 44 having a proximal end 46 and a distal end 48. Catheter 14 may also include other conventional components not illustrated herein such as a temperature sensor, additional electrodes, and corresponding conductors or leads. The connector 40 provides mechanical and electrical connection (s) for cable 56 extending from signal generator 26. The connector 40 may include conventional components known in the art and, as shown, is disposed at the proximal end of catheter 14.

Handle 42 provides a location for the clinician to hold catheter 14 and may further provide means for steering or guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, or orientation of a portion of the catheter. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced, retracted and/or steered or guided through body 17 to a desired location such as the site of tissue 16, including through the use of guidewires or other means known in the art.

In some embodiments, catheter 14 is a hoop catheter (shown, for example, in FIGS. 2 and 3), sometimes referred to as a spiral or loop catheter, having catheter electrodes distributed about one or more hoops at the distal end of shaft 44. The diameter of the hoop(s) (sometimes referred to herein as "loops") may be variable. In some embodiments, the hoop catheter diameter is variable by about ten millimeters (mm) between a minimum diameter and a maximum diameter. The minimum diameter in some embodiments may be selected between about thirteen mm and about twenty mm when the catheter 14 is manufactured. With a ten mm range of variability, such catheters would have a maximum diameter between twenty-three mm and thirty mm. In other embodiments, the hoop diameter is variable between about fifteen mm and about twenty-eight mm, between about thirteen mm and about twenty-three mm, or between about seventeen mm and about twenty-seven mm. Alternatively, the catheter may be a fixed diameter hoop catheter or may be variable between different diameters. In some embodiments, catheter 14 has fourteen catheter electrodes (e.g., grouped as seven pairs of catheter electrodes). In other embodiments, catheter 14 includes ten catheter electrodes, twenty catheter electrodes, or any other suitable number of electrodes for performing, for example, sensing, mapping, diagnostics, or ablation. In some embodiments, the catheter electrodes are ring electrodes. Alternatively, the catheter electrodes may be any other suitable type of electrodes, such as single sided electrodes or electrodes printed on a flex material. In various embodiments, the catheter electrodes have lengths of 1.0 mm, 2.0 mm, 2.5 mm, and/or any other suitable length for sensing, mapping, diagnostics, or ablation.

Figure 2:
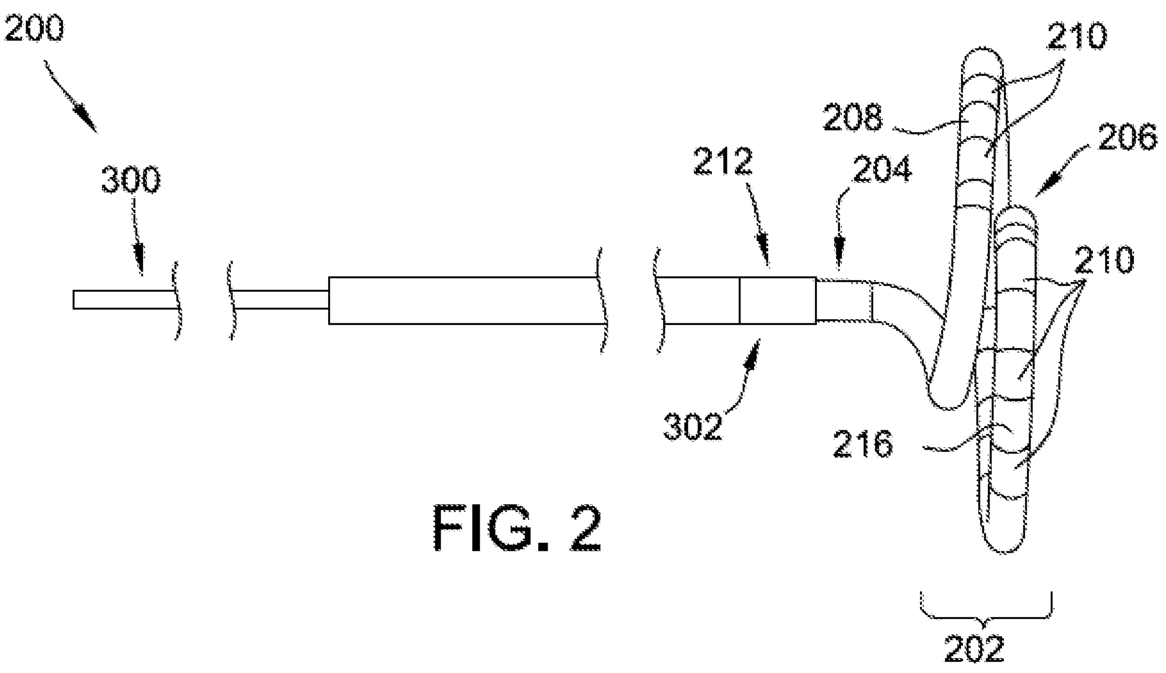
FIG. 2 is a side view of an example electrode assembly suitable for use in the system of FIG. 1, illustrated in the form of an electrode loop assembly.
Figure 3:
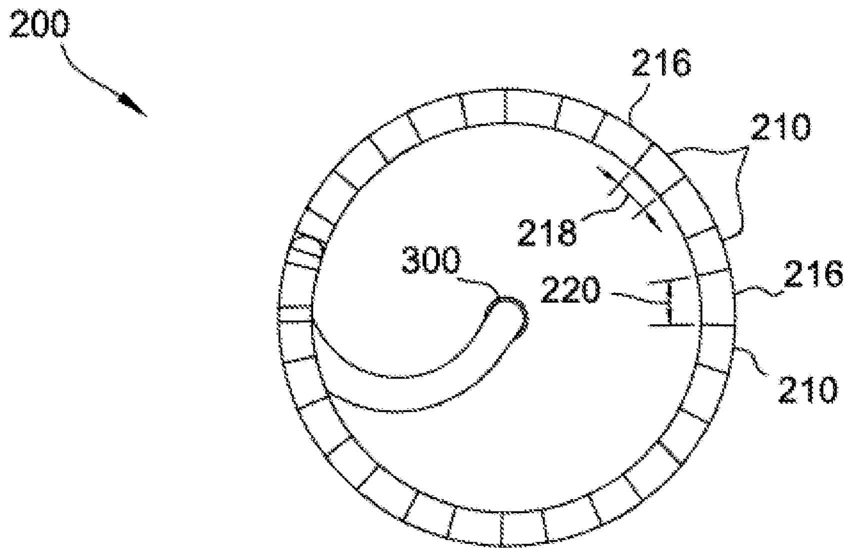
FIG. 3 is an end view of the electrode loop assembly of FIG. 2.

FIGS. 2 and 3 illustrate an exemplary electrode assembly 12 suitable for use in system 10, illustrated in the form of an electrode hoop or loop assembly 200. FIG. 2 is a side view of electrode loop assembly 200 with a variable diameter loop 202 coupled at the distal end 302 of a catheter shaft 300. FIG. 3 is an end view of variable diameter loop 202 of electrode loop assembly 200. As shown in FIGS. 2 and 3, electrode loop assembly 200 extends from a proximal end 204 to a distal end 206, and includes an outer sleeve 208 formed in the shape of a loop, and a plurality of catheter electrodes 210 mounted on outer sleeve 208. Proximal end 204 of electrode loop assembly 200 is coupled to catheter shaft 300 via a suitable coupler 212. Electrodes 210 may be used for a variety of diagnostic and therapeutic purposes including, for example and without limitation, cardiac sensing, mapping, diagnostics, or ablation (e.g., IRE). For example, electrode loop assembly 200 may be configured as a monopolar electrode assembly for use in monopolar-based electroporation therapy. In such embodiments, ground pad 18 may function as the return electrode.

In other embodiments, electrode loop assembly 200 may be configured as a bipolar electrode assembly. More specifically, electrodes 210 may be configured as electrode pairs (e.g., cathode-anode electrode pairs) and electrically coupled to signal generator 26 (e.g., via suitable electrical wire or other suitable electrical conductors extending through catheter shaft 44) such that adjacent electrodes 210 are energized with opposite polarities to generate a potential and corresponding electric field between adjacent electrodes 210. In other embodiments, any combination of electrodes 210 may be configured as electrode pairs (e.g., cathode-anode electrode pairs), including, for example and without limitation, adjacent electrodes, non-adjacent electrodes, and any other combination of electrodes that enables system 10 to function as described herein. As described above, for example, signal generator 26 and/or computer system 32 may selectively energize certain electrodes 210 of electrode loop assembly 200 to form electrode pairs based on contact between electrodes 210 and tissue 16.

In the illustrated embodiment, variable diameter loop 202 includes fourteen catheter electrodes 210 evenly spaced around the circumference of variable diameter loop 202. In other embodiments, variable diameter loop 202 may include any suitable number of catheter electrodes 210 made of any suitable material. Each catheter electrode 210 is separated from each other catheter electrode by an insulated gap 216. In the example embodiment, each catheter electrode 210 has a same length 218 (shown in FIG. 3) and each insulated gap 216 has a same length 220 as each other gap 216. Length 218 and length 220 are both about 2.5 mm in the example embodiment. In other embodiments, length 218 and length 220 may be different from each other. Moreover, in some embodiments, catheter electrodes 210 may not all have the same length 218 and/or insulated gaps 216 may not all have the same length 220. In some embodiments, catheter electrodes 210 are not spaced evenly around the circumference of variable diameter loop 202.

It should be understood that electrode assembly 12 is not limited to the specific constructions shown and described herein, and may include any other suitable electrode assembly and have any other suitable construction that enables system 10 to function as described herein. By way of example, electrode assembly 12 may have the same or similar construction as electrode assemblies described in U.S. Pat. Nos. 10,136,829, 10,750,975, U.S. Pat. Application Publication No. 2019/0201688, U.S. patent application Ser. No. 17/247,198, U.S. Provisional Patent Application No. 63/192,723, and International Patent Application Publication Nos. WO2018/208795, WO2020/251857, and WO2020/227086, the disclosures of which are incorporated herein by reference in their entirety.

Referring again to FIG. 1, visualization, navigation, and/or mapping system 30 may include commercially available systems, including electric field-based or magnetic-based systems such as the EnSite™ Velocity™ or EnSite Precision™ cardiac mapping and visualization systems of Abbott Laboratories. Visualization, navigation, and/or mapping system 30 may additionally include an impedance-based localization feature such as, for example, the NAVX™ system also commercially available with the EnSite™ Velocity™ or EnSite Precision™ systems from Abbott Laboratories, and as generally shown with reference to U.S. Pat. No. 7,263,397 titled "Method and Apparatus for Catheter Navigation and Location and Mapping in the Heart," the entire disclosure of which is incorporated herein by reference. Visualization, navigation, and/or mapping system 30 may include hybrid mapping and navigation systems such as, for example, the EnSite™ X cardiac mapping system from Abbott Laboratories, which includes integrated impedance and magnetic tracking. In other exemplary embodiments, the visualization, navigation, and/or mapping system 30 can comprise other types of systems, such as, for example and without limitation: a magnetic field-based system such as the CARTO System (now in a hybrid form with impedance- and magnetically-driven electrodes) available from Biosense Webster, or the gMPS system from MediGuide Ltd. In accordance with a combination electric field-based and magnetic field-based system, the catheter can include both electrodes as impedance-based electrodes and one or more magnetic field sensing coils. Commonly available fluoroscopic, computed tomography (CT), and magnetic resonance imaging (MRI)-based systems can also be used.

System 10 may include a variable impedance 27. The variable impedance may be used to change one or more characteristics, such as amplitude, duration, pulse shape, and the like, of an output of signal generator 26 or visualization, navigation, and/or mapping system 30. Although described as a separate component, variable impedance 27 may be integrated with catheter 14 or signal generator 26 and visualization, navigation, and/or mapping system 30. Variable impedance 27 includes one or more impedance elements, such as resistors, capacitors, or inductors (not shown) connected in series, parallel, or combinations of series and/or parallel. In the illustrated embodiment, the variable impedance is connected in series with catheter 14. Alternatively, the impedance elements of variable impedance 27 may be connected in parallel with catheter 14 or in a combination of series and parallel with catheter 14. Moreover, in other embodiments, the impedance elements of the variable impedance are connected in series and/or parallel with ground pad 18. Some embodiments include more than one variable impedance, each of which may include one or more impedance elements. In such embodiments, each variable impedance may be connected to a different catheter electrode or group of catheter electrodes to allow the impedance through each catheter electrode or group of catheter electrodes to be independently varied. In other embodiments, the impedance of system 10 may not need to be varied and the variable impedance may be omitted.

The relatively high voltages and short pulse durations of the biphasic waveforms generated by signal generator 26 may result in significant electromagnetic interference (EMI), or noise, being introduced into signal generator 26, its components, catheter 14, or tissue 16 of the patient, and potentially adversely affecting operation of system 10. Accordingly, embodiments of the present disclosure include certain features to reduce sources of noise and to mitigate the effects of the high frequency high voltage switching within signal generator 26 for the purpose of producing the high-amplitude short duration pulses.

For example, FIG. 4 is a schematic diagram of exemplary signal generator 26. Signal generator 26 includes a microcontroller 402 or other programmable processing device that controls generation of one or more biphasic pulse in response to a trigger signal 404. Trigger signal 404 may be generated internal to signal generator 26 or externally by another system. In certain embodiments, the trigger signal is a discrete logic-level DC signal supplied to microcontroller 402 as a result of, for example, an at least momentary closure of a switching circuit by a switch or button actuated by a user. In response to trigger signal 404, microcontroller 402 initiates a single pulse, a burst of pulses, or a plurality of bursts, for example.

Microcontroller 402, in generating a single biphasic pulse, generates a first pulse control signal 406 and a second pulse control signal 408 for the purpose of controlling a plurality of semiconductor switches. First pulse control signal 406 and second pulse control signal 408 are logic level DC signals generated by microcontroller 402. The semiconductor switches may be any suitable power semiconductor capable of a high-voltage standoff, high current conduction, and operable at a high frequency, such as an insulated-gate bipolar transistor (IGBT). In the embodiment of FIG. 4, the semiconductor switches are implemented as IGBTs 410, 412, 414, 416 connected in a bridge configuration to regulate application of positive high voltage DC (+HVDC) supply 418 and negative high voltage DC (−HVDC) supply 420 to one or more conductors such as first or second conductors 422 or 424 that deliver the biphasic pulses using, for example, electrode assembly 12 and a return electrode, such as ground pad 18. Microcontroller 402, in generating a burst of biphasic pulses, controls IGBTs 410, 412, 414, 416 to commutate at a frequency (e.g., in the range of about 20 hertz to about 110 KHz) to produce a series of biphasic pulses. The biphasic pulses, in certain embodiments, may be delivered over one conductor to one or more monopolar electrodes. For example, the biphasic pulses are delivered over first conductor 422 while second conductor 424 is connected to a return electrode such as, or in addition to, ground pad 18 and serves as a return path for the current delivered by first conductor 422. Alternatively, biphasic pulses may be delivered over first and second conductors 422 and 424 to one or more pairs of bipolar electrodes.

Microcontroller 402 is communicatively coupled and electrically isolated from IGBTs 410, 412, 414, 416 by an opto-isolator 426. Opto-isolator 426, also referred to as an opto-coupler, prevents, for example, noise generated by high frequency switching of IGBTs 410, 412, 414, 416 from reaching microcontroller 402. Opto-isolator 426 relays first pulse control signal 406 and second pulse control signal 408 from microcontroller 402 to a logic circuit 428 that translates the two logic level DC signals into four gate driving signals 430, 432, 434, 436. Logic circuit 428 derives each of gate driving signals 430, 432, 434, 436 from first pulse control signal 406 and second pulse control signal 408, and ensures that gate driving signals 430, 432, 434, 436 do not connect, or short, the opposite-polarity HVDC supplies (+HVDC supply 418 and −HVDC supply 420), for example, momentarily during a transition from a +HVDC phase to a-HVDC phase of the biphasic pulse. For example, in certain embodiments, logic circuit 428 derives gate driving signals 434 and 436 as inversions of gate driving signals 430 and 432.

Generally, in at least some embodiments, microcontroller 402 does not source sufficient current to drive the gates of IGBTs 410, 412, 414, 416. Gate current for power semiconductor switches typically rises with high voltage and high current capacity. Accordingly, signal generator 26 includes gate drivers 438, 440, 442, 444 for operating IGBTs 410, 412, 414, 416, respectively. Gate drivers 438, 440, 442, 444 further isolate microcontroller 402 and other aspects of the digital circuit from the high-voltage high-current portions of signal generator 26. Gate drivers 438, 440, 442, 444 control commutation of IGBTs 410, 412, 414, 416 according to gate driving signals 430, 432, 434, 436. Gate drivers 438, 440, 442, 444 drive gates of IGBTs 410, 412, 414, 416 through gate driving impedances 446, 448, 450, 452. Gate driving impedances 446, 448, 450, 452 are selected both to produce a sufficient current rise through IGBTs 410, 412, 414, 416 and to avoid oscillatory responses by IGBTs 410, 412, 414, 416. In certain embodiments, gate driving impedances 446, 448, 450, 452 are resistors in the range of 6-8 ohms. In at least some embodiments, gate driving impedances 446, 448, 450, 452 are 6.8 ohm resistors.

Signal generator 26 may be implemented, in certain embodiments, on one or more printed circuit boards (PCBs) on which microcontroller 402, opto-isolator 426, logic circuit 428, gate drivers 438, 440, 442, 444, and IGBTs 410, 412, 414, 416 may be disposed. At least some traces on the PCB conduct high-voltage DC that is switched at a high frequency. For example, traces connecting +HVDC supply 418 to IGBTs 410, 412, 414, 416, and traces supplying current from IGBTs 410, 412, 414, 416 to terminals 456 and 458 for first and second conductors 422 and 424 each carry the pulses generated by high-frequency switching of IGBTs 410, 412, 414, 416, and thus are susceptible to introducing noise to signal generator 26. In certain embodiments, such traces should be sufficiently wide and as short as possible to reduce the introduction of noise resulting from the periodic high di/dt conditions on those traces. In certain embodiments, these traces should be at least 0.12 inches wide. Likewise, at least some traces conduct significant amounts of high-frequency switched current for the purpose of driving gates of IGBTs 410, 412, 414, 416. For example, traces extending between gate drivers 438, 440, 442, 444 and their respective IGBTs 410, 412, 414, 416 are each also susceptible to introducing noise resulting from high di/dt conditions on those traces. Accordingly, those traces should also be sufficiently wide and as short as possible to reduce the introduction of noise. In certain embodiments, for example, the traces between gate drivers 438, 440, 442, 444 and their respective IGBTs 410, 412, 414, 416 should be at least 0.06 inches wide.

In certain embodiments, signal generator 26 includes additional components between each of gate drivers 438, 440, 442, 444 and IGBTs 410, 412, 414, 416. For example, in certain embodiments, one or more capacitors are coupled in parallel with the gate of the semiconductor switch to function as a current supply for driving that gate. In certain embodiments, one or more diodes are coupled in parallel with the gate of the semiconductor switch to function, for example, as transient voltage suppression or as current blocking devices. In certain embodiments, one or more EMI suppression devices are coupled to the gate driving branch to mitigate noise originating from, for example, high frequency switching of IGBTs 410, 412, 414, 416.

In certain embodiments, signal generator 26 includes one or more impedance matching circuits (not shown) connected in series with the high-voltage DC output, i.e., in series with first and second conductors 422 and 424. The impedance matching circuits mitigate impedance discontinuities that may occur or that may be inherent at various portions of the high-voltage DC transmission line formed by the traces or other conductors between +HVDC supply 418, −HVDC supply 420, and electrode assembly 12 of catheter 14. For example, an impedance discontinuity may exist where catheter 14 connects to signal generator 26, which may result in signal reflections within signal generator 26 that ultimately manifest as noise and losses in system 10.

Signal generator 26 is configured to energize the electrode element(s) in accordance with an electroporation energization strategy, which may be predetermined or may be user-selectable. For electroporation-induced primary necrosis therapy, signal generator 26 may be configured to produce an electric current that is delivered via electrode assembly 12 as a pulsed electric field in the form of a biphasic IRE waveform transmitted from one or more monopolar electrodes and utilizing, for example, ground pad 18 or another patch electrode as a return path. In alternative embodiments, the biphasic IRE waveform is transmitted between closely spaced electrodes (e.g., electrode pairs of electrode assembly 12). The biphasic IRE waveform is capable of delivering an electric field strength of about 0.1 to 1.0 kV/cm (e.g., at the tissue site). Biphasic pulses generated by signal generator 26 are specifically shaped (e.g., by controlling the phases, amplitude, and pulse duration) to prevent activation of skeletal muscles and nerves (e.g., Phrenic nerve), as well as the myocardium. By avoiding activation of the myocardium, the biphasic pulses generated by signal generator 26 do not have to be timed or gated based on the cardiac cycle or rhythm (e.g., along the R-wave). More specifically, biphasic pulses generated by signal generator 26 are shaped to have a pulse width and voltage amplitude below the strength-duration curve associated with nerve or muscle activation. The biphasic pulses generated by signal generator 26 are relatively high strength (i.e., voltage) and frequency (i.e., short pulse duration). Cardiac tissue, for example, needs electric field strength of 400 V/cm to damage the cellular membrane. In generating a biphasic IRE pulse, in some embodiments, signal generator 26 provides +HVDC supply 418 at a potential of about zero VDC to 3000 VDC and −HVDC supply 420 may be at a potential of about zero VDC to −3000 VDC. Alternatively, signal generator 26 may provide +HVDC supply 418 and −HVDC supply 420 at potentials having magnitudes greater than 3000 VDC, for example, up to 3500 VDC, 4000 VDC, or greater. Signal generator 26, in at least some embodiments, includes at least one high-voltage capacitor 454 to function as the high voltage current source for electrode assembly 12.

Figure 5:
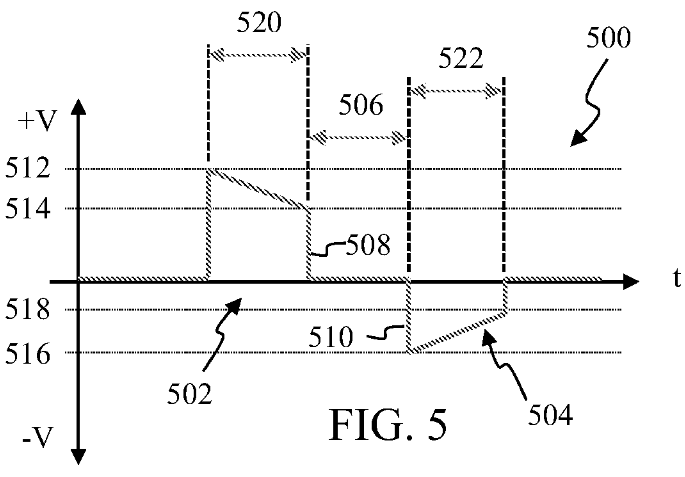
FIG. 5 is a plot of an example biphasic IRE pulse.

FIG. 5 is a plot of an example biphasic IRE pulse 500 produced by signal generator 26. Biphasic IRE pulse 500 is illustrated as a voltage (shown on a vertical axis) versus time (shown on a horizontal axis). Biphasic IRE pulse 500 includes a first phase 502 and a second phase 504, with an interphase delay 506 between a trailing edge 508 of the first phase 502 and a leading edge 510 of the second phase 504. The interphase delay 506 should be brief enough to effectively reverse current conduction in the tissue of the patient to avoid stimulating or damaging non-target tissue. For example, the interphase delay 506 is in the range of 100 ns to 100 us. In certain embodiments, the interphase delay 506 is in the narrower range of 20 us to 25 us.

First phase 502 and second phase 504 have different voltage amplitudes or different pulse widths, or both. For example, first phase 502 has an initial voltage amplitude 512 that decays over the duration of first phase 502 as capacitor 454 discharges through the patient load. First phase 502 has an ending voltage amplitude 514 before falling to zero at the beginning of interphase delay 506. The peak voltage amplitude, e.g., the initial voltage amplitude 512, should be large enough to create a lesion-depth large enough to be durable in the target tissue, e.g., in an atrium or ventricle. Initial voltage amplitude 512 is in the range of 1000 VDC to 3000 VDC. Likewise, an initial voltage amplitude 516 of second phase 504 is in the range of −1000 VDC to −3000 VDC, and decays over the duration of second phase 504 to an ending voltage amplitude 518. In certain embodiments, initial voltage amplitude 512 and initial voltage amplitude 516 are different, and a pulse width 520 of first phase is about equal to a pulse width 522 of second phase 504. Alternatively, pulse width 520 and pulse width 522 may be different, while initial voltage amplitude 512 and initial voltage amplitude 516 are about equal, or different.

Catheter 14 supplies the biphasic IRE pulse 500, for example, over first conductor 422 coupled to one or more monopolar electrodes of electrode assembly 12. In such an embodiment, second conductor 424 may be coupled to a patch electrode that functions as a return path for the current delivered in biphasic IRE pulse 500. Alternatively, first conductor 422 may be referenced to ground using ground pad 18. The polarity of the high voltage pulse can be alternated by alternating application of +HVDC supply 418 and −HVDC supply 420 to first conductor 422. A zero VDC is achieved, e.g., during interphase delay 506, by disconnecting both +HVDC supply 418 and −HVDC supply 420 from first conductor 422, and allowing its potential to float relative to second conductor 424 (or ground pad 18). Given the conductive properties of a blood/saline solution in the body 17 of the patient, there should be no potential between electrodes of electrode assembly 12 and second conductor 424 (or ground pad 18), and thus no potential between first conductor 422 and second conductor 424 (or ground pad 18).

In an example embodiment, first phase 502 of biphasic IRE pulse 500 begins with initial voltage amplitude 512 between about 1000 VDC and 2000 VDC, and second phase 504 begins with initial voltage amplitude 516 roughly equal in magnitude or less than ending voltage amplitude 514, or about 500 VDC to 1750 VDC. In certain embodiments, +HVDC supply 418 provides a potential between 1000 VDC and 2000 VDC, and −HVDC supply 420 provides a potential between 500 VDC and 1750 VDC, and a monopolar electrode coupled to first conductor 422 utilizes ground pad 18 as a return path for current delivered by biphasic IRE pulse 500. For example, where +HVDC supply 418 is at a potential of about 2000 VDC and −HVDC supply 420 is at a potential of about-1750 VDC, first phase 502 of biphasic IRE pulse 500 is produced by closing IGBT 410 and opening IGBT 414 to apply +HVDC supply 418 to first conductor 422 producing a +2000 VDC signal for a first duration, e.g., pulse width 520. The voltage amplitude applied to first conductor 422 decays over pulse width 520 from initial voltage amplitude 512 to ending voltage amplitude 514, or about 1750 VDC. After the first duration, IGBT 410 and IGBT 412 are opened to allow the potential of first conductor 422 to float, thereby producing zero VDC for the duration of interphase delay 506. After interphase delay 506, IGBT 414 is closed to apply-HVDC supply 420 to first conductor 422. At that time, the initial voltage amplitude 516 for second phase 504 is generally equal in magnitude or less than ending voltage amplitude 514, e.g., about 1750 VDC. The initial voltage amplitude 516 further decays over the duration of second phase 504, i.e., pulse width 522, to ending voltage amplitude 518. IGBT 414 is opened to return the potential of first conductor 422 to 0 VDC.

In one alternative embodiment, second conductor 424 is utilized as a return path for current delivered in biphasic IRE pulse 500 via a monopolar electrode coupled to first conductor 422. In such an embodiment, the potential delivered in the biphasic IRE waveform 500 is a differential between first conductor 422, regulated by IGBT 410 and 414, and second conductor 424, regulated by IGBT 412 and 416.

In certain embodiments, high voltage capacitor 454 may be initially charged by +HVDC supply 418, e.g., to about 2000 VDC, and functions as a current supply for both first phase 502 and second phase 504. High voltage capacitor 454 may be partially discharged over the duration of first phase 502, e.g., pulse width 520, to ending voltage amplitude 514. High voltage capacitor 454 may be further discharged during second phase 504, but with a reversed polarity achieved by "re-referencing," or reconfiguring a plurality of switches (not shown) through which high voltage capacitor 454 is coupled to first conductor 422 and ground. Accordingly, initial voltage amplitude 516 for second phase 504 is roughly equal in magnitude to ending voltage amplitude 514 of first phase 502, which is the remaining charge on high voltage capacitor 454 after first phase 502. In certain embodiments, the magnitude of initial voltage amplitude 516 may be reduced further by "bleeding off," during interphase delay 506, some energy stored in high voltage capacitor 454, resulting in a reduced charge on high voltage capacitor 454 at the beginning of second phase 504. For example, if ending voltage amplitude 514 is about 1750 VDC, high voltage capacitor 454 may be discharged to about 1500 VDC during interphase delay 506, resulting in initial voltage amplitude 516 of about 1500 VDC.

In an alternative embodiment, catheter 14 supplies the biphasic IRE pulse 500, for example, over first and second conductors 422 and 424 to one or more pairs of bipolar electrodes of electrode assembly 12. Accordingly, the polarity of the high voltage signal can be switched by alternatingly applying, in time, +HVDC supply 418 to first conductor 422 and second conductor 424, and −HVDC supply 420 to second conductor 424 and first conductor 422. Likewise, 0 VDC is achieved by disconnecting both first and second conductors 422 and 424 and allowing their potential to float. Consequently, due to the conductive properties of a blood/saline solution in the body 17 of the patient, there should be no potential between electrodes of electrode assembly 12, and thus no potential between first and second conductors 422 and 424.

Figure 6:
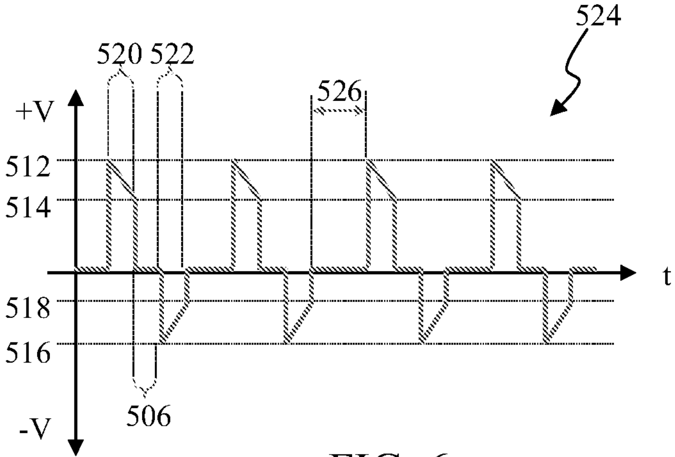
FIG. 6 is a plot of an example burst of biphasic IRE pulses.
Figure 7:
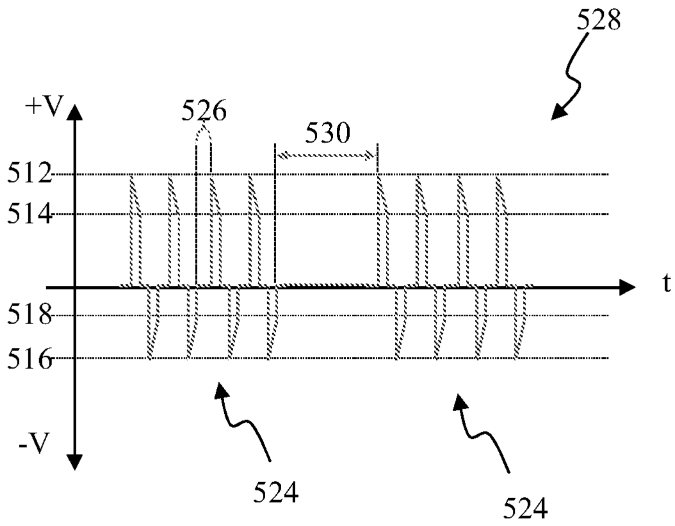
FIG. 7 is a plot of an example biphasic IRE waveform having multiple bursts.

FIG. 6 is a plot of an example burst 524 of biphasic IRE pulses 500 shown in FIG. 5. Burst 524 includes four instances of biphasic IRE pulse 500 separated by an interpulse delay 526. Although FIG. 6 illustrates burst 524 with four biphasic IRE pulses 500, burst 524 may include any number of biphasic IRE pulses 500. Interpulse delay 526 is in the range of 9 us to 50 ms. In certain embodiments, interpulse delay 526 is in the range of 20 us to 50 us. FIG. 7 is a plot of an example biphasic IRE waveform 528 having multiple bursts 524 of biphasic IRE pulses 500. Each burst 524 is separated by an interburst delay 530 in a range of 270 us to 10 s. Although FIG. 7 illustrates biphasic IRE waveform 528 having two bursts 524, biphasic IRE waveform 528 may have any number of bursts 524, each with any number of biphasic IRE pulses 500.

Figure 8:
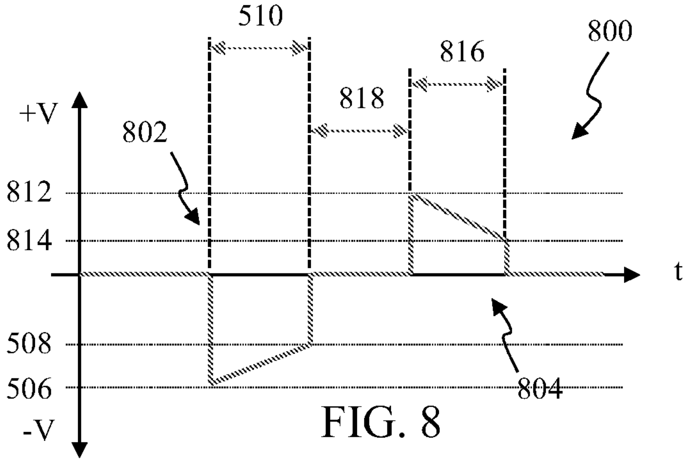
FIG. 8 is a plot of an example inverted biphasic IRE pulse.

FIG. 8 is a plot of an example inverted biphasic IRE pulse 800 having a first phase 802 that is negative in polarity, and a second phase 804 that is positive in polarity. First phase 802 has an initial voltage amplitude 806 decaying to an ending voltage amplitude 808 over a pulse width 810. Likewise, second phase 804 has an initial voltage amplitude 812 decaying to an ending voltage amplitude 814 over a pulse width 816. First phase 802 is separated from second phase 804 by an interphase delay 818.

Figure 9:
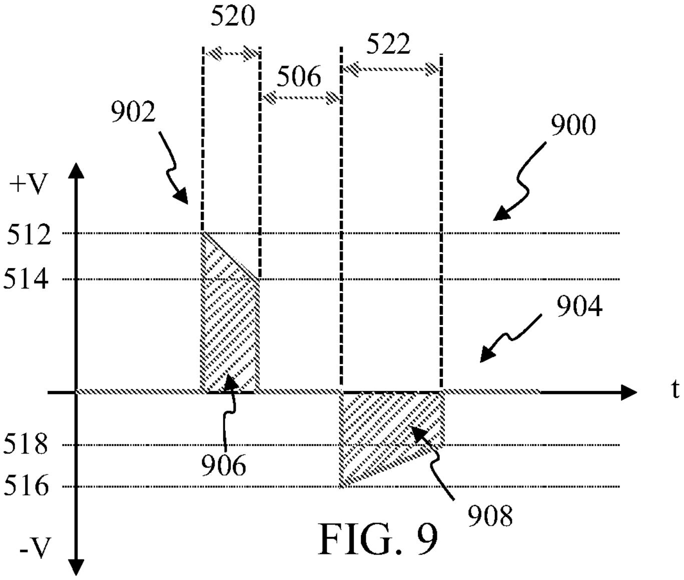
FIG. 9 is a plot of another example of a biphasic IRE pulse.

FIG. 9 is a plot of another example of a biphasic IRE pulse 900 having a first phase 902 and a second phase 904. Similar to biphasic IRE pulse 500, first phase 902 and second phase 904 are separated by interphase delay 506. First phase 902 has a pulse width 520 and a peak voltage amplitude, or initial voltage amplitude 512, and ending voltage amplitude 514. Second phase 904 has a pulse width 522 and a peak voltage amplitude, or initial voltage amplitude 516, and ending voltage amplitude 518. Notably, an area 906 under first phase 902 is about equal to an area 908 under second phase 904. Areas 906 and 908 relate to an aggregate applied charge, or energy delivered, to the tissue of the patient over the duration of first phase 902 and second phase 904. For example, as illustrated in FIG. 9, pulse width 520 is shorter in duration than pulse width 522, and that difference is offset by first phase 902 having higher voltage amplitudes 512 and 514 than voltage amplitudes 516 and 518 of second phase 904. In alternative embodiments, area 908 under second phase 904 is a percentage of area 906 under first phase 902. For example, in one embodiment, area 908 is 75% of area 906 under first phase 902. In another embodiment, area 908 is 120% of area 906 under first phase 902.

Figure 10:
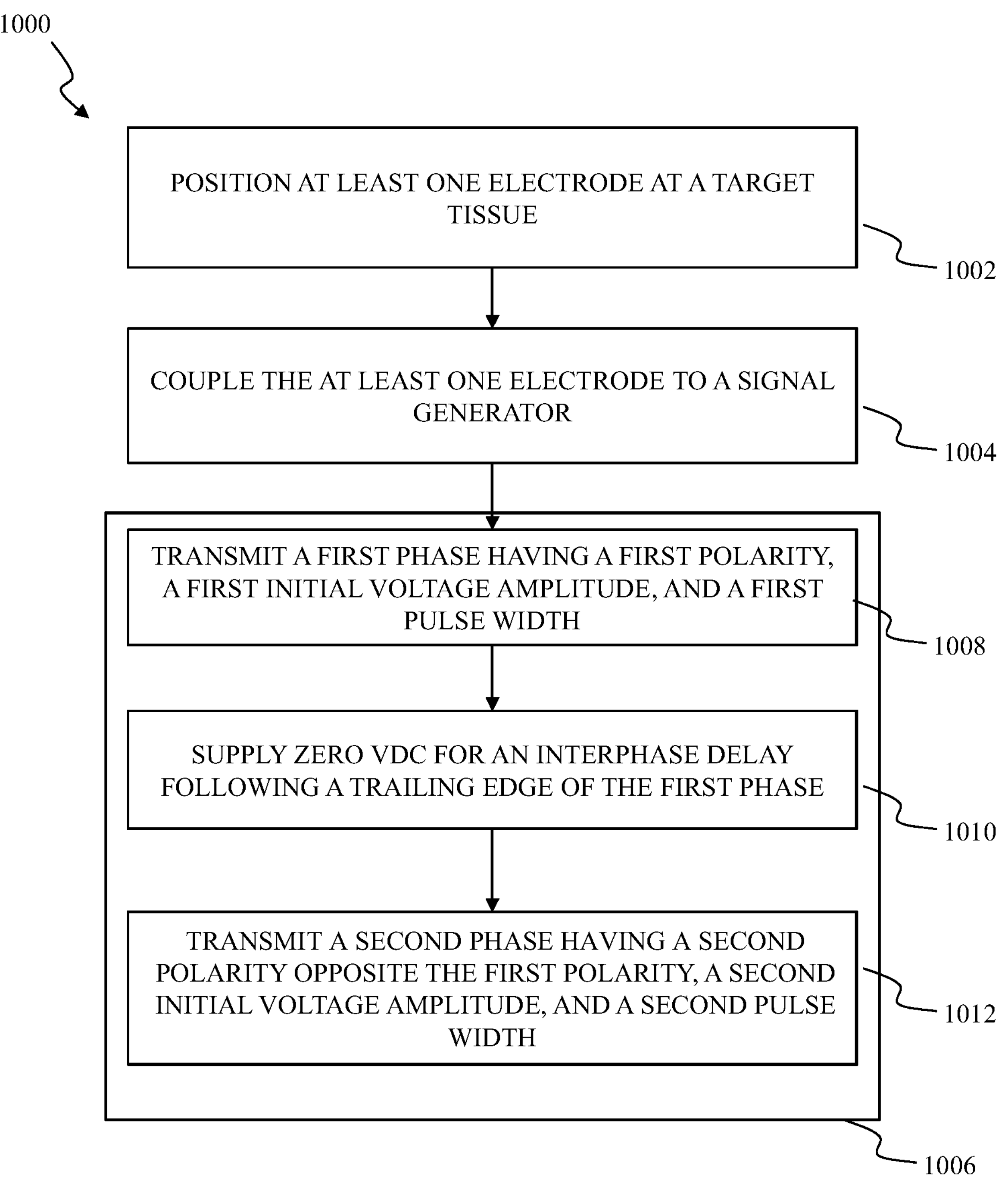
FIG. 10 is a flow diagram of an example method of delivering electroporation energy through an ablation catheter.

FIG. 10 is a flow diagram of an example method 1000 of delivering electroporation energy through an ablation catheter, such as catheter 14 shown in FIG. 1. Catheter 14 and at least one electrode are positioned 1002 at target tissue 16. The electrode is coupled 1004 to signal generator 26. Signal generator 26 supplies 1006 a biphasic pulse, such as biphasic pulse 500 shown in FIG. 5. Supplying 1006 the biphasic pulse 500 includes transmitting 1008 first phase 502 having a first polarity (e.g., positive), a first initial voltage amplitude 512, and a first pulse width 520. Signal generator 26 then supplies 1010 zero VDC during interphase delay 506 following a trailing edge 508 of first phase 502. Signal generator 26 then transmits 1012 second phase 504 having a second polarity opposite the first polarity (e.g., negative), a second initial voltage amplitude 516, and a second pulse width 522. At least one of the first initial voltage amplitude 512 or the first pulse width 520 is different from the second initial voltage amplitude 516 or the second pulse width 522, respectively. That is, either first initial voltage amplitude 512 and second initial voltage amplitude 516 are of different magnitude, or first pulse width 520 and second pulse width 522 are different, or both.

Although certain steps of the example method are numbered, such numbering does not indicate that the steps must be performed in the order listed. Thus, particular steps need not be performed in the exact order they are presented, unless the description thereof specifically requires such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

Some embodiments involve the use of one or more electronic processing or computing devices. As used herein, the term "microcontroller" and related terms, e.g., "processor," "computer," "processing device," "computing device," and "controller," are not limited to just those integrated circuits referred to in the art as a computer, but broadly refer to a processor, a processing device, a controller, a general purpose central processing unit (CPU), a graphics processing unit (GPU), a microcontroller, a microcomputer, a programmable logic controller (PLC), a reduced instruction set computer (RISC) processor, a field programmable gate array (FPGA), a digital signal processing (DSP) device, an application specific integrated circuit (ASIC), and other programmable circuits or processing devices capable of executing the functions described herein, and these terms may be used interchangeably herein. These processing devices are generally "configured" to execute functions by programming or being programmed, or by the loading or other provisioning of instructions for execution. The above examples are not intended to limit in any way the definition or meaning of the terms processor, processing device, and related terms.

In the embodiments described herein, memory may include, but is not limited to, a non-transitory computer-readable medium, such as flash memory, a random access memory (RAM), read-only memory (ROM), erasable programmable read-only memory (EPROM), electrically erasable programmable read-only memory (EEPROM), and non-volatile RAM (NVRAM). As used herein, the term "non-transitory computer-readable media" is intended to be representative of any tangible, computer-readable media, including, without limitation, non-transitory computer storage devices, including, without limitation, volatile and non-volatile media, and removable and non-removable media such as a firmware, physical and virtual storage, CD-ROMs, DVDs, and any other digital source such as a network or the Internet, as well as yet to be developed digital means, with the sole exception being a transitory, propagating signal. Alternatively, a floppy disk, a compact disc-read only memory (CD-ROM), a magneto-optical disk (MOD), a digital versatile disc (DVD), or any other computer-based device implemented in any method or technology for short-term and long-term storage of information, such as, computer-readable instructions, data structures, program modules and sub-modules, or other data may also be used. Therefore, the methods described herein may be encoded as executable instructions, e.g., "software" and "firmware," embodied in a non-transitory computer-readable medium. Further, as used herein, the terms "software" and "firmware" are interchangeable, and include any computer program stored in memory for execution by personal computers, workstations, clients and servers. Such instructions, when executed by a processor, cause the processor to perform at least a portion of the methods described herein.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An electroporation system comprising:

a catheter shaft;

at least one electrode coupled to the catheter shaft at a distal end thereof; and a signal generator coupled in communication with the at least one electrode, the signal generator configured to supply a biphasic pulse to the at least one electrode, the biphasic pulse comprising:

a first phase having a first polarity, a first initial voltage amplitude, a first pulse width, and a first ending voltage amplitude; and a second phase having a second polarity, a second initial voltage amplitude, a second pulse width, and a second ending voltage amplitude, wherein the first initial voltage amplitude is different from the first ending voltage amplitude or the second initial voltage amplitude is different from the second ending voltage amplitude;

wherein a first area of the first phase and a second area of the second phase are about equal.

2. The electroporation system of claim 1, wherein the first initial voltage amplitude and the second initial voltage amplitude are in a range of 1000 volts direct current (VDC) to 3000 VDC.

3. The electroporation system of claim 1, wherein the first pulse width and the second pulse width are in a range of 100 nanoseconds to 200 microseconds.

4. The electroporation system of claim 1, wherein the first pulse width and the second pulse width are in a range of 5 microseconds to 10 microseconds.

5. The electroporation system of claim 1, comprising an interphase delay in a range of 100 nanoseconds to 100 microseconds.

6. The electroporation system of claim 1, comprising an interphase delay in a range of 20 microseconds to 25 microseconds.

7. The electroporation system of claim 1, wherein the signal generator is further configured to supply a first burst of a plurality of biphasic pulses, wherein a leading edge of a second biphasic pulse occurs after an interpulse delay following a trailing edge of a first biphasic pulse.

8. The electroporation system of claim 7, wherein the interpulse delay is in a range of 9 microseconds to 50 milliseconds.

9. The electroporation system of claim 7, wherein the interpulse delay is in a range of 20 microseconds to 50 microseconds.

10. The electroporation system of claim 7, wherein the signal generator is further configured to supply a second burst of a second plurality of biphasic pulses after an interburst delay following the first burst.

11. The electroporation system of claim 10, wherein the interburst delay is in a range of 270 microseconds to 10 seconds.

12. The electroporation system of claim 1, wherein the first polarity and the second polarity are opposite to each other.

13. The electroporation system of claim 12, wherein:

the first initial voltage amplitude decays to the first ending voltage amplitude; and the second initial voltage amplitude decays to the second ending voltage amplitude.

14. The electroporation system of claim 1, wherein:

the first initial voltage amplitude and the first ending voltage amplitude differ from each other; and the second initial voltage amplitude and the second ending voltage amplitude differ from each other.

15. A method of delivering electroporation energy through an ablation catheter, the method comprising:

positioning at least one electrode at a target tissue;

coupling the at least one electrode to a signal generator;

supplying, by the signal generator, a biphasic pulse, the supplying comprising:

transmitting a first phase having a first polarity, a first initial voltage amplitude, a first pulse width, and a first ending voltage amplitude; and transmitting a second phase having a second polarity, a second initial voltage amplitude, a second pulse width, and a second ending voltage amplitude, wherein the first initial voltage amplitude differs from the first ending voltage amplitude or the second initial voltage amplitude differs from the second ending voltage amplitude, and wherein a first area of the first phase and a second area of the second phase are about equal.

16. The method of claim 15, wherein the first initial voltage amplitude and the second initial voltage amplitude are in a range of 1000 volts direct current (VDC) to 3000 VDC.

17. The method of claim 15, wherein the first pulse width and the second pulse width are in a range of 100 nanoseconds to 200 microseconds.

18. The method of claim 15, wherein the first pulse width and the second pulse width are in a range of 5 microseconds to 10 microseconds.

19. The method of claim 15, comprising an interphase delay is in a range of 100 nanoseconds to 100 microseconds.

20. The method of claim 15, comprising an interphase delay in a range of 20 microseconds to 25 microseconds.

21. The method of claim 15 further comprising generating a first burst of a plurality of biphasic pulses, wherein a leading edge of a second biphasic pulse occurs after an interpulse delay following a trailing edge of a first biphasic pulse.

22. The method of claim 21, wherein the interpulse delay is in a range of 9 microseconds to 50 milliseconds.

23. The method of claim 21, wherein the interpulse delay is in a range of 20 microseconds to 50 microseconds.

24. The method of claim 21 further comprising generating a second burst of a second plurality of biphasic pulses after an interburst delay following the first burst.

25. The method of claim 24, wherein the interburst delay is in a range of 270 microseconds to 10 seconds.

26. A signal generator for electroporation therapy, the signal generator comprising:

a voltage supply configured to supply a first voltage direct current (VDC) having a first polarity and a second VDC having a second polarity opposite the first polarity;

a plurality of semiconductor switches configured to regulate application of the first VDC and the second VDC to a conductor and electrode of an ablation catheter; and a microcontroller communicatively coupled to the plurality of semiconductor switches and configured to control commutation of the plurality of semiconductor switches to transmit a biphasic pulse through the conductor and electrode, the biphasic pulse comprising:

a first phase having the first polarity, a first initial voltage amplitude, a first pulse width, and a first ending voltage amplitude; and a second phase having the second polarity, a second initial voltage amplitude, a second pulse width, and a second ending voltage amplitude, wherein the first initial voltage amplitude differs from the first ending voltage amplitude or the second initial voltage amplitude of differs from the second ending voltage amplitude, wherein a first area of the first phase and a second of the second phase are about equal.

* * * * *